US010441237B2

(12) United States Patent
Bertens

(10) Patent No.: US 10,441,237 B2
(45) Date of Patent: Oct. 15, 2019

(54) MOTION CORRECTION METHOD IN DUAL ENERGY RADIOGRAPHY

(71) Applicant: AGFA NV, Mortsel (BE)

(72) Inventor: Tom Bertens, Mortsel (BE)

(73) Assignee: AGFA NV, Morstel (BE)

( * ) Notice: Subject to any disclaimer, the term of this patent is extended or adjusted under 35 U.S.C. 154(b) by 204 days.

(21) Appl. No.: 15/536,346

(22) PCT Filed: Dec. 15, 2015

(86) PCT No.: PCT/EP2015/079757
§ 371 (c)(1),
(2) Date: Jun. 15, 2017

(87) PCT Pub. No.: WO2016/096833
PCT Pub. Date: Jun. 23, 2016

(65) Prior Publication Data
US 2017/0340305 A1 Nov. 30, 2017

(30) Foreign Application Priority Data
Dec. 16, 2014 (EP) .................................... 14198241

(51) Int. Cl.
*A61B 6/00* (2006.01)
*G06T 7/33* (2017.01)
*G06T 7/00* (2017.01)

(52) U.S. Cl.
CPC ............ *A61B 6/5264* (2013.01); *A61B 6/482* (2013.01); *A61B 6/5235* (2013.01); *G06T 7/0012* (2013.01); *G06T 7/33* (2017.01); *G06T 7/337* (2017.01); *A61B 6/505* (2013.01); *G06T 2207/10116* (2013.01); *G06T 2207/30008* (2013.01); *G06T 2207/30061* (2013.01)

(58) Field of Classification Search
USPC .......... 250/363.03; 345/419, 633; 348/208.6, 348/402.1, 699; 378/65; 382/103, 106, 382/113, 130, 132, 181, 218, 254, 290, 382/294
See application file for complete search history.

(56) References Cited

U.S. PATENT DOCUMENTS 5,689,306 A * 11/1997 Jung ...................... H04N 19/54
348/699
5,690,106 A * 11/1997 Bani-Hashemi ....... A61B 6/481
382/130

(Continued)

OTHER PUBLICATIONS

Official Communication issued in International Patent Application No. PCT/EP2015/079757, dated Feb. 5, 2016.

*Primary Examiner* — Xuemei G Chen
(74) *Attorney, Agent, or Firm* — Keating and Bennet, LLP

(57) ABSTRACT

A motion correction method includes two steps. The first step includes a global motion correction using the bilinear warping technique and a rough delineation of the lung fields. One of the native images (low energy image, high energy image) is deformed to match the other image. In a second step, local motion corrections are applied to the globally motion corrected image by computing a proximity value in small overlapping tiles. Only tiles with a sufficient high proximity value are taken into account. The maximum shift applied in this second step is limited to a few pixels to avoid strong deformations of the native images.

12 Claims, 3 Drawing Sheets

(56) References Cited

U.S. PATENT DOCUMENTS

| | | | | |
|---|---|---|---|---|
| 5,784,431 A * | 7/1998 | Kalend | | G06K 9/6211 378/65 |
| 5,982,915 A * | 11/1999 | Doi | | G06T 3/0081 382/130 |
| 6,157,747 A * | 12/2000 | Szeliski | | G06K 9/209 345/419 |
| 7,068,826 B2 * | 6/2006 | Jabri | | A61B 6/405 382/128 |
| 7,257,245 B2 | 8/2007 | Oosawa | | |
| 7,869,667 B1 * | 1/2011 | Wu | | G06K 9/4609 382/113 |
| 8,005,288 B2 * | 8/2011 | Chen | | G06T 5/005 382/132 |
| 8,073,230 B2 * | 12/2011 | Fei | | A61B 6/12 382/132 |
| 8,155,452 B2 * | 4/2012 | Minear | | G06T 7/32 382/181 |
| 8,798,387 B2 * | 8/2014 | Yamada | | H04N 5/23254 382/254 |
| 8,842,936 B2 * | 9/2014 | Kawamura | | G06T 3/0068 382/294 |
| 9,202,284 B2 * | 12/2015 | Akiyama | | G06T 7/246 |
| 9,345,443 B2 * | 5/2016 | Bertens | | A61B 6/032 |
| 9,367,928 B2 * | 6/2016 | de Almeida Barreto | | G06T 11/001 |
| 9,584,824 B2 * | 2/2017 | Wang | | H04N 19/56 |
| 9,886,645 B2 * | 2/2018 | Pitts | | G06K 9/4671 |
| 2003/0048949 A1 * | 3/2003 | Bern | | G06K 9/342 382/218 |
| 2003/0142787 A1 | 7/2003 | Jabri et al. | | |
| 2004/0252230 A1 * | 12/2004 | Winder | | H04N 5/145 348/402.1 |
| 2007/0196007 A1 | 8/2007 | Chen et al. | | |
| 2007/0206880 A1 | 9/2007 | Chen et al. | | |
| 2008/0247626 A1 | 10/2008 | Dhanantwari et al. | | |
| 2008/0265166 A1 * | 10/2008 | Shekhar | | G01T 1/1611 250/363.03 |
| 2011/0222781 A1 * | 9/2011 | Nguyen | | G06K 9/6244 382/218 |
| 2012/0162454 A1 * | 6/2012 | Park | | H04N 5/145 348/208.6 |
| 2014/0003690 A1 | 1/2014 | Razeto et al. | | |
| 2014/0169627 A1 * | 6/2014 | Gupta | | G06K 9/00805 382/103 |
| 2014/0225919 A1 * | 8/2014 | Kaino | | G06T 19/006 345/633 |
| 2015/0170367 A1 * | 6/2015 | Nachman | | G06K 9/00671 382/106 |
| 2017/0091550 A1 * | 3/2017 | Feng | | G06K 9/00597 |

* cited by examiner

Template

Image Patch

Translation offset -1,-1

Proximity measure

Translation offset -1,1

Translation offset 0,1

MOTION CORRECTION METHOD IN DUAL ENERGY RADIOGRAPHY

CROSS REFERENCE TO RELATED APPLICATIONS

This application is a 371 National Stage Application of PCT/EP2015/079757, filed Dec. 15, 2015. This application claims the benefit of European Application No. 14198241.3, filed Dec. 16, 2014, which is incorporated by reference herein in its entirety.

BACKGROUND OF THE INVENTION

1. Field of the Invention

The invention relates to dual energy radiography and more particularly to a motion correction method to reduce misregistration artifacts in tissue type specific derivative images.

2. Description of the Related Art

The diagnostic reading of chest examinations is impeded by anatomical noise. Thoracic abnormalities are hard to recognize due to obstruction by overlying bone structures. In standard chest radiography the contrast of the bone structures is partly reduced by taking exposures with high-energy photons (ca. 120 kVp).

The technique of dual energy subtraction allows separating bone and soft tissue by using a dual exposure: one with a high energy spectrum and one with a low energy spectrum. The outcome is a standard posterior-anterior chest image and 2 tissue-type specific images. This technique aids in identifying and characterizing nodules, masses, lung diseases and bone abnormalities.

Although the two exposures are made within less than a second (typically 200 ms) motion artifacts from respiration, heart motion and physiological motion requires a motion correction method to reduce the motion artifacts.

The overlapping structures in the projection radiographic images can show different displacements. For example the motion due to respiration is complex and structures in the lung fields (e.g. the bronchi) can move into other directions compared to the overlapping rib structures. Even the shadows of the anterior ribs and posterior ribs can show different displacements.

To optimize the quality of the soft tissue derivative image, it is important to suppress the bone structures. Motion artifacts due to misalignment of the bone structures are disturbing and must be avoided. However the displacement of soft tissue in the images must be taken into account to avoid strong deformations of the soft tissue areas.

A proposal for a soft tissue type driven image registration method is described in U.S. Pat. No. 7,257,245 B2. The method relies on mask images indicating tissue type specific structures in the high energy (HE) and the low energy (LE) image to steer the image alignment. This approach strongly depends on the ability to identify corresponding tissue type specific structures in the dual exposure native images.

SUMMARY OF THE INVENTION

Preferred embodiments of the present invention provide a method for correction of motion in a dual energy image recording process that overcomes the above-described disadvantages.

The above-mentioned aspects are realised by a method having the method steps set out below.

Specific features for preferred embodiments of the invention are also set out below.

The present invention is generally implemented as a computer program product adapted to carry out the method of any of the claims when run on a computer and is stored on a computer readable medium.

Further advantages and embodiments of the present invention will become apparent from the following description and drawings.

DETAILED DESCRIPTION OF THE PREFERRED EMBODIMENTS

In dual energy radiography 2 images are generated by an x-ray imaging system: a low energy native image (LE) and a high energy native image (HE).

A log-subtraction technique allows decomposing the low and high energy native images into material specific images, e.g. a bone and soft tissue image in chest radiography, using a simplified physical model that does not take into account spatially dependent effects as the heel effect, beam hardening and scatter:

$$P_{OUT} = \mathrm{Exp}(\mathrm{Log}(P_H) - w\mathrm{Log}(P_L))$$
$$= \mathrm{Exp}(-\mu_{S,H}z_S - \mu_{B,H}z_B - w(-\mu_{S,L}z_S - \mu_{B,L}z_B))$$
$$= \mathrm{Exp}(-(\mu_{S,H} - w\mu_{S,L})z_S - (\mu_{B,H} - w\mu_{B,L})z_B)$$

With $\mu_{S,L}$ and $\mu_{B,L}$ the attenuation coefficients of soft tissue and bone for the low-energy spectrum, $\mu_{S,H}$ and $\mu_{B,H}$ the attenuation coefficients of soft tissue and bone for the high-energy spectrum and $z_S$ and $z_B$ the thicknesses of soft tissue and bone in the patient for pixel position (x, y).

By choosing the appropriate weight parameters w, a soft tissue image can be reconstructed ($w=w_B=\mu_{B,H}/\mu_{B,L}$) and a bone image can be reconstructed ($w=w_S=\mu_{S,H}/\mu_{S,L}$).

In case of a dual-exposure system, the low and high energy native images must be spatially registered to reduce misalignment artifacts due to cardiac, respiratory, bowel and patient motion.

Preprocessing operations can be applied to the low and high energy image to reduce the noise, remove the anti-scatter grid line-artifacts, etc.

According to a preferred embodiment of the present invention, motion correction is achieved by applying a global motion correction step to one of the low energy or high energy native images followed by a local motion correction step applied to the globally motion corrected (intermediate) image.

The global motion correction is based on bilinear warping of one of the low energy or high energy native images controlled by a number of control points.

In a specific embodiment the radiographic image is a chest image.

Figure 1:
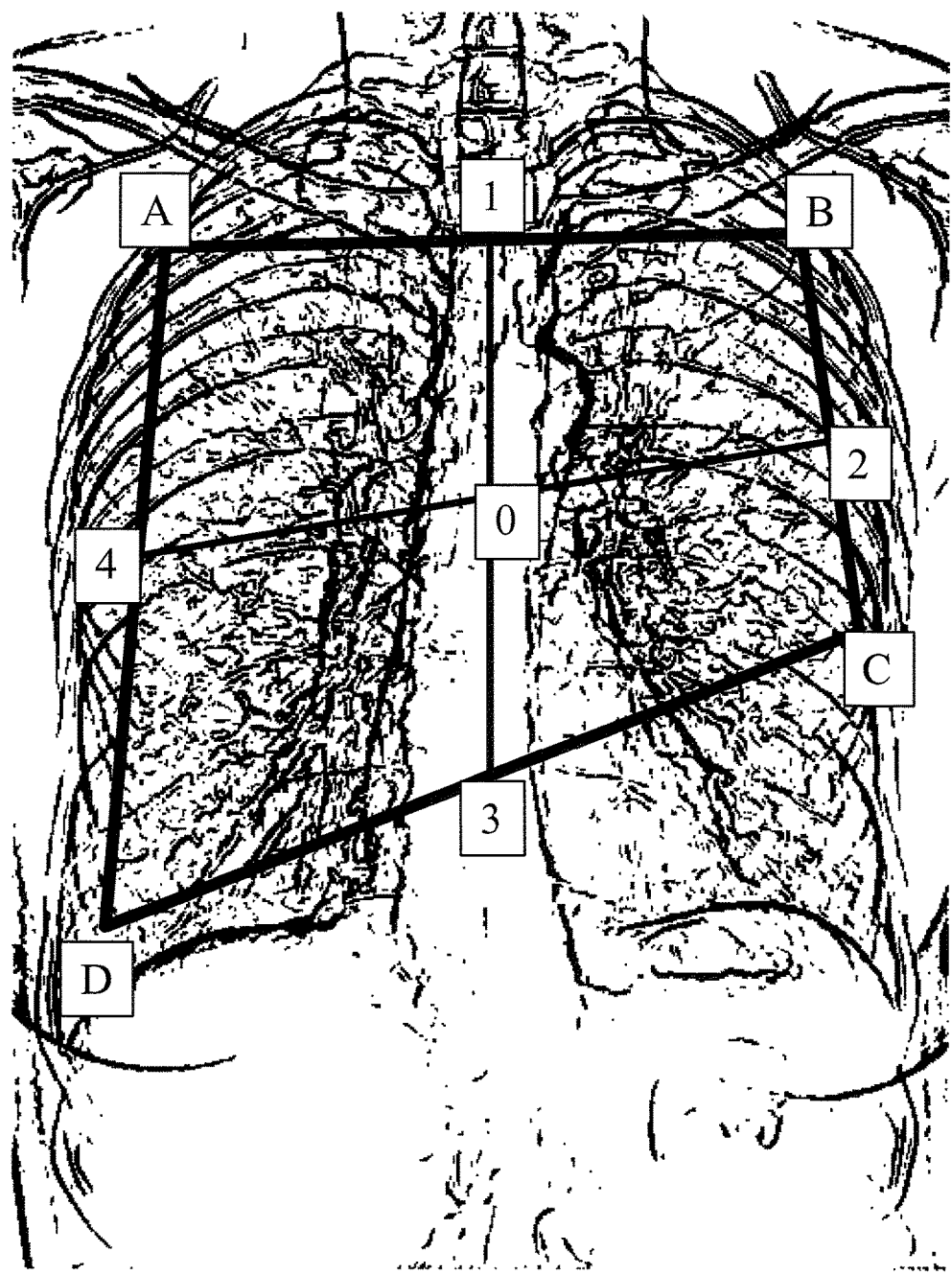
FIG. 1 shows a quadrangle fitted to the lung fields.

In this embodiment these control points are the 4 control points, more specifically 4 corners of a quadrangle that roughly delineates the lung fields in the chest image (see FIG. 1, points A, B, C, D).

These corner control points are found by analyzing horizontal and vertical average profiles of one of the native images.

The corner control points are chosen near the edge of the lung fields.

At the periphery of the lung fields, the motion of the shadows of bone structures and soft tissue are more or less aligned. Moreover the discrepancy between the displacements of the anterior and posterior ribs is limited in this region. So near the edge of the lung fields local motion can accurately be computed taking into account all the pixels.

Figure 2:
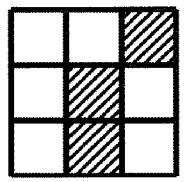
FIG. 2 shows the local proximity measure for multiple translation offsets.
Figure 2:
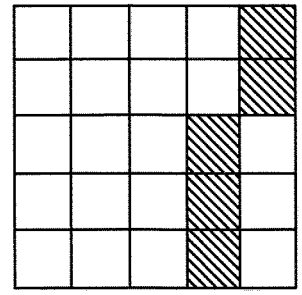
Figure 2:
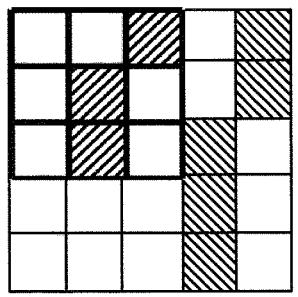
Figure 2:
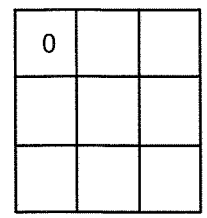
Figure 2:
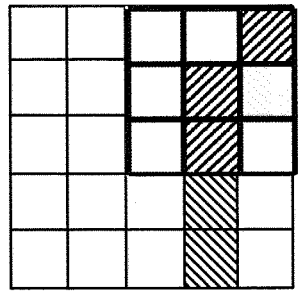
Figure 2:
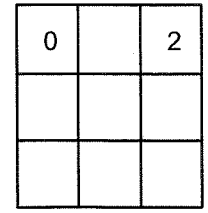
Figure 2:
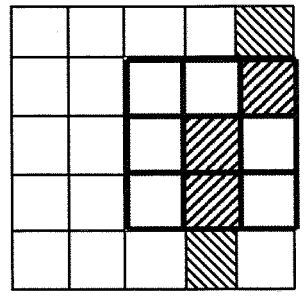
Figure 2:
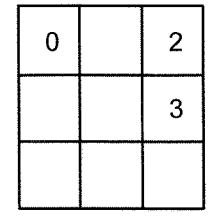

At these corner control points the local proximity value between the dual exposure native images (High energy (HE) image and low energy (LE) image) is computed for multiple translation offsets using local image patches centred at the corner control points (as illustrated in FIG. 2).

There are several ways to compute the local proximity (also called similarity) between images.

In a preferred embodiment the local proximity value is the (normalized) cross-correlation coefficient of a patch in one of the low or high energy native images (e.g. the low energy native image) and a template of the other native image (e.g. the high energy native image) for multiple translation offsets.

An implementation of the normalized cross-correlation coefficient calculation is described in "Fast Normalized Cross-Correlation", J. P. Lewis, Vision Interface, 1995.

$$\gamma(u, v) = \frac{\sum_{x,y}[f(x,y) - \overline{f}_{u,v}][t(x-u, y-v) - \overline{t}]}{\left\{\sum_{x,y}[f(x,y) - \overline{f}_{u,v}]^2 \sum_{x,y}[t(x-y, y-u) - \overline{t}]^2\right\}^{0.5}}$$

Where
t is the template
$\overline{t}$ is the mean of the template
f is the image patch
$\overline{f}_{u,v}$ is the mean of the image patch under the region of the template In a specific embodiment, the images are multiplicatively demodulated. In a typical implementation, the multiplicative demodulation of the dual exposure input images is performed by dividing the original pixel values by its low pass filtered version. The multiplicative demodulated images are preferably clipped to limit the impact of high signal contrasts to the proximity value.

In a preferred embodiment the size of the template is a square with a physical extent between 3 cm and 6 cm. The template is shifted over a maximum distance of 4 mm in every direction.

In another embodiment the proximity value is computed directly on the grey value native images using the normalized cross-correlation coefficient.

In still another embodiment the Euclidean distance or mutual information can be used as proximity values.

In every control point the translation offset for which the proximity value reaches its maximum value and exceeds a predefined threshold is chosen as displacement vector. Thresholding avoids introducing unreliable displacement vectors due to noise contamination in the native images. The chosen threshold is related to the expected noise level in the native images.

To improve the robustness, the maximum proximity value and corresponding displacement vector can be computed in additional control points. In a preferred embodiment the additional control points are the midpoints of the pairs (A,B), (B,C), (C,D), (A,D) and the centre of quadrangle ABCD (see FIG. 1, points 0 to 4).

Control points 0, 1 and 3 are located near the spine. Taking into account these additional control points will avoid unwanted deformations in the centre of the image.

In a preferred embodiment the final position and displacement of the 4 corners of the quadrangle ABCD are computed as weighted average using the position and displacement of each corner control point and 3 additional control points with the shortest distance to the said corner control point.

Figure 3:
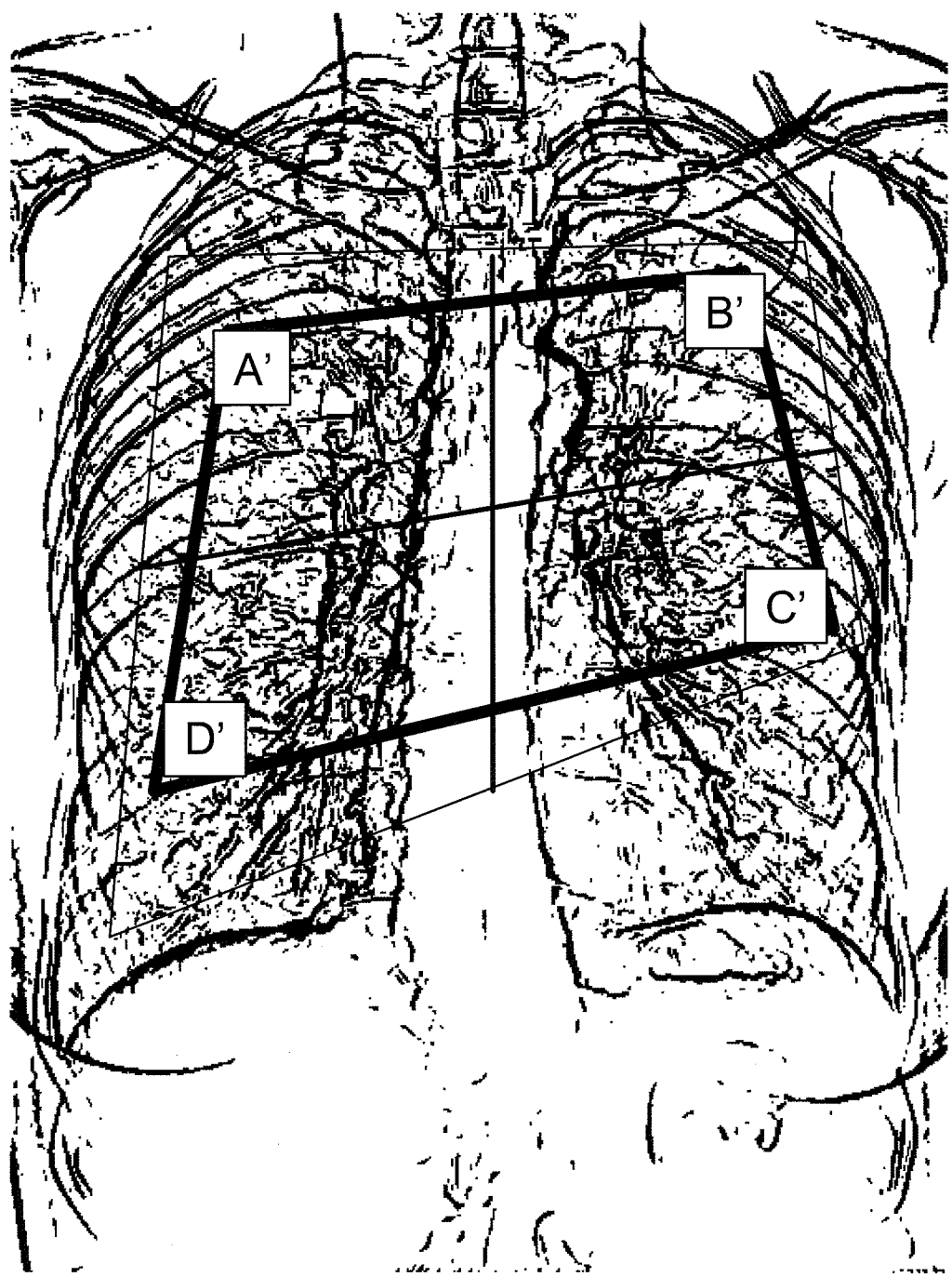
FIG. 3 shows the actual (final) corner control points.

This results in a new quadrangle with corner points A', B', C' and D' (see FIG. 3).

The position of these corner points A', B', C' and D' and the corresponding final displacements are computed using as following combinations:
A' based on A, 0, 1 and 4
B' based on B, 0, 1 and 2
C' based on C, 0, 2 and 3
D' based on D, 0, 3 and 4

In a preferred embodiment the weights assigned to the different control points are determined by the proximity values and a predefined weight distribution.

Only control points with a proximity value above a predefined threshold are taken into account. The weight distribution over the different control points ensures that the weight of a corner control points is at least twice the weight of the additional control points.

Given the positions of the corner points A', B', C' and D' and the corresponding displacements, the motion correction is applied using warping, e.g. bilinear warping.

Bilinear warping transforms pixel coordinates (x,y) in the original image to new coordinates (x', y') according to the formulas:

$$x' = a_0 + a_1 * x * y + a_2 * x + a_3 * y$$

$$y' = b_0 + b_1 * x * y + b_2 * x + b_3 * y$$

The 8 unknown coefficient $a_x$ and $b_x$ can be computed out of the given x and y coordinates and displacements of the 4 corner points A', B', C' and D' using well known matrix algebra operations.

The pixel values of the warped image are computed using interpolation such as cubic interpolation.

In a second step the (bilinear) warped image is locally corrected for further improving the content matching with the other, non-modified native image.

To compute the local displacements, proximity values are computed using overlapping tiles in the globally corrected image and a non globally correct (high or low energy) native image. The tiles are computed for every N-th pixel in horizontal and vertical direction. A typical value for N is 16.

In a preferred embodiment the local value of proximity is the normalized cross-correlation coefficient of a tile in the warped image, e.g. bilinear warped low energy image and a template of the other native image (e.g. the HE image) for multiple translation offsets or vice-versa. (Images may be multiplicatively demodulated similar as described with regard to the global correction steps).

Typical tile size is 63×63 pixels. Translation offsets are preferably limited to shifts in both directions of maximum 2 pixels.

The translation offset for which the proximity value reaches its maximum value and exceeds a predefined threshold is chosen as local displacement vector.

The result is a sparse sampled local motion correction displacement map.

The displacement vector for each intermediate pixel is computed using bilinear interpolation of the values in the sparse displacement map.

In another embodiment cubic interpolation is used to compute the displacement vectors for each intermediate pixel.

The local motion correction displacement map is applied to the globally corrected image (e.g. the bilinear warped LE image) using bilinear interpolation.

In another embodiment cubic interpolation is used to apply the displacement map to the (bilinear) warped (LE) image.

The motion corrected dual exposure images are used to compute tissue type specific images with suppressed motion artifacts.

Such a method to compute the tissue type specific images is the calibration free dual energy radiography method as described in patent application WO/2013/037659.

Post-processing operations can be applied to the tissue type specific images to reduce noise, to apply scatter corrections and to convert the pixel values to values suitable for reproduction or displaying, e.g. using known multiscale image processing methods as there are multiscale gradation processing (EP1341125) and multiscale contrast enhancement processing (EP1347413).

The invention claimed is:

1. A method for correcting motion artifacts in a dual energy radiography image, the method comprising the steps of:
   correcting a global position to globally correct positions of pixels in at least one of a high energy radiographic native image and a low energy radiographic native image of a same subject to obtain a globally corrected image; and
   after the step of correcting the global position, correcting a local position to locally correct pixel positions in the globally corrected image; wherein
   the step of correcting the global position includes:
      determining, for pre-defined control points in one of the high energy radiographic native image and the low energy radiographic native image, a local proximity value for multiple translation offsets using local image patches centered at the pre-defined control points;
      deriving a displacement vector for each of the pre-defined control points from the determined local proximity values;
      deducing warping coefficients for a warping transformation from the displacement vectors; and
      applying the warping transformation to one of the high energy radiographic native image and the low energy radiographic native image to obtain the globally corrected image; and
   the step of correcting the local position of the globally corrected image includes:
      defining overlapping tiles in the globally corrected image and a non-globally corrected high energy radiographic native image or a non-globally corrected low energy radiographic native image;
      computing local displacement vectors for each of the overlapping tiles;
      using the local displacement vectors to build a displacement map; and
      applying the displacement map to the globally corrected image.

2. The method according to claim 1, wherein the warping transformation is a bilinear warping transformation.

3. The method according to claim 1, wherein the dual energy radiography image is a chest image and the control points are corner points of a quadrangle substantially delineating a lung field in the chest image.

4. The method according to claim 1, further comprising defining and using additional control points to derive the displacement vector.

5. The method according to claim 1, wherein the displacement vector is a translation offset for which the local proximity value obtained for the multiple translation offsets reaches a maximum and exceeds a predefined threshold.

6. The method according to claim 5, wherein the local proximity value is a cross correlation coefficient of an image patch centered at a corner point in one of the high energy radiographic native image and the low energy radiographic native image and a template of the other of the high energy radiographic native image and the low energy radiographic native image.

7. The method according to claim 6, wherein at least one of the high energy radiographic native image and the low energy radiographic native image is multiplicatively demodulated.

8. The method according to claim 5, wherein the local proximity value is defined as a cross correlation coefficient of an image patch in the globally corrected image and a template of the non-globally corrected high energy radiographic native image or the non-globally corrected low energy radiographic native image.

9. The method according to claim 8, wherein at least one of the globally corrected image and the non-globally corrected high energy radiographic native image or non-globally corrected low energy radiographic native image is multiplicatively demodulated.

10. The method according to claim 1, wherein the local displacement vector for each pixel is computed by applying interpolation to values of the displacement map.

11. The method according to claim 1, wherein the displacement map is applied to the globally corrected image using bilinear interpolation.

12. A non-transitory computer readable medium comprising computer executable program code adapted to carry out, when the computer executable program code is executed on a computer, the steps of:
   correcting a global position to globally correct positions of pixels in at least one of a high energy radiographic native image and a low energy radiographic native image of a same subject to obtain a globally corrected image; and
   after the step of correcting the global position, correcting a local position to locally correct pixel positions in the globally corrected image; wherein
   the step of correcting the global position includes:
      determining, for pre-defined control points in one of the high energy radiographic native image and the low energy radiographic native image, a local proximity value for multiple translation offsets using local image patches centered at the pre-defined control points;

deriving a displacement vector for each of the predefined control points from the determined local proximity values;
deducing warping coefficients for a warping transformation from the displacement vectors; and
applying the warping transformation to one of the high energy radiographic native image and the low energy radiographic native image to obtain the globally corrected image; and the step of correcting the local position of the globally corrected image includes:
defining overlapping tiles in the globally corrected image and a non-globally corrected high energy radiographic native image or a non-globally corrected low energy radiographic native image;
computing local displacement vectors for each of the overlapping tiles;
using the local displacement vectors to build a displacement map; and
applying the displacement map to the globally corrected image.

* * * * *